United States Patent [19]

Ward

[11] 4,032,626

[45] June 28, 1977

[54] REAGENT AND METHOD FOR TBG ASSAY

[75] Inventor: Frank B. Ward, Painted Post, N.Y.

[73] Assignee: Corning Glass Works, Corning, N.Y.

[22] Filed: June 30, 1976

[21] Appl. No.: 701,193

[52] U.S. Cl. .................................. 424/1; 424/12; 23/230 B; 23/230.6

[51] Int. Cl.² .................. G01N 33/00; A61K 39/00

[58] Field of Search ................. 424/1, 1.5, 12; 23/230 B, 230.6

[56] References Cited

UNITED STATES PATENTS

| | | | |
|---|---|---|---|
| 3,933,997 | 1/1976 | Hersh et al. | 424/1 |
| 3,960,492 | 6/1976 | DiGiulio | 23/230 B |
| 3,975,511 | 8/1976 | Vann et al. | 424/1.5 |

Primary Examiner—Brooks H. Hunt
Assistant Examiner—Christine M. Nucker
Attorney, Agent, or Firm—James A. Giblin; Clinton S. Janes, Jr.; Clarence R. Patty, Jr.

[57] ABSTRACT

The concentration of thyroxine binding globulin (TBG) in a fluid sample can be determined via radioassay technique with an immunochemical composite comprising anti-TBG antibodies immobilized on a water-insoluble carrier. The composite is incubated with the sample in a quantity sufficient to assure complexation of substantially all TBG in the sample to the antibodies of the composite. The quantity of TBG complexed is determined with radiolabeled thyroxine ($T_4$) which complexes with at least a portion of the complexed TBG. By separating the labeled composite from the remaining labeled $T_4$, and counting the bound (or unbound) $T_4$, the concentration of TBG can be determined from a standard curve.

11 Claims, 2 Drawing Figures

REAGENT AND METHOD FOR TBG ASSAY

BACKGROUND OF THE INVENTION

This disclosure relates generally to a method of determining the concentration of a substance using radiolabeled materials and specifically to a method of determining the concentration of thyroxine binding globulin in a fluid sample using radiolabeled thyroxine ($T_4$) and immobilized anti-TBG antibodies.

The diagnosis of dysfunction of the thyroid gland and related organs and systems is greatly facilitated by the rapid and accurate assay of various serum hormones such as triiodothyronine ($T_3$), thyroxine ($T_4$), thyrozine stimulating hormone (TSH) and certain globulins such as thyroxine binding globulin (TBG). Various methods of assaying such constituents are well known. Present systems for the assay of TBG in human serum, however, are non-quantitative (i.e. $T_3$ uptake test) or consist of classical RIA procedures having attendent disadvantages (i.e. intrinisically labeled antigens).

Quite surprisingly, it has been found that by modifying certain radioassay techniques and using such modifications with a novel reagent consisting of immobilized anti-TBG antibodies, a relatively quick and simple method of determining TBG concentrations is possible. Details of the method are described herein.

SUMMARY OF THE INVENTION

The reagent useful for determining the concentration of TBG in a liquid sample comprises an immunochemical composite consisting of antiTBG antibodies immobilized on the surfaces of a high surface area, essentially water insoluble carrier material. In a preferred embodiment the composite comprises anti-TBG antibodies fixed onto the surfaces of an inorganic carrier such as suspendable glass particles. In use, the composite is incubated with a fluid sample such as blood serum under conditions sufficient to assure complexation of substantially all sample TBG with the anti-TBG antibodies of the suspendable composite. Radiolabeled $T_4$ (e.g. $I^{125}$ labeled $T_4$) is made available to complex with at least a portion of the TBG, thereby providing a labeled composite, the amount of radioactivity of which is related to the TBG present. In a preferred embodiment, the total incubation time for both reactions is less than about 60 minutes. After a portion of the TBG is so labeled, the labeled composite is separated from the excess (or unbound) labeled $T_4$ and counted for radioactivity. The count can be correlated with TBG concentration using a standard cure prepared by known means.

SPECIFIC EMBODIMENTS

Figure 1:
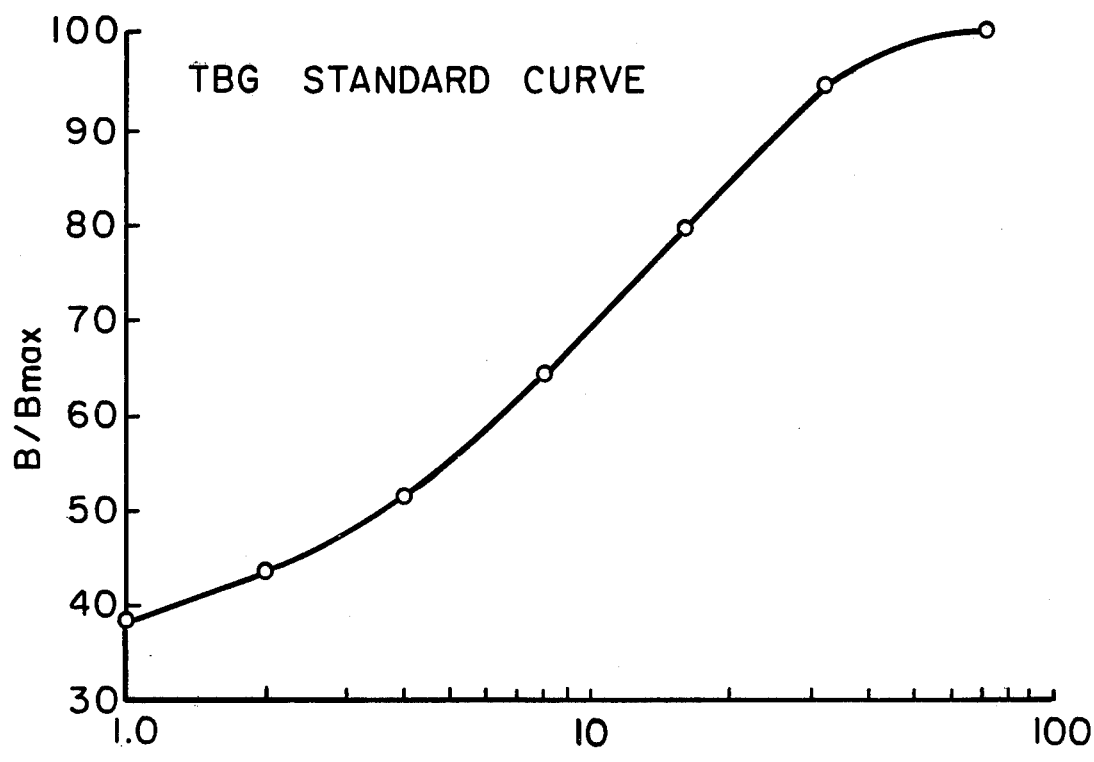
FIG. 1 illustrates a typical standard curve for determining TBG values according to the method disclosed.

Very important to the method of determining TBG concentration is the immobilized antibodies to TBG. The antibodies can be obtained by conventional methods known to those skilled in the art. The anti-TBG antiserum used to prepare the composites described herein is described as a anti-human thyroxine binding globulin which was obtained by immunization of New Zealand white rabbits. The anti-serum thus obtained and used in the examples had a titer of about 1:20,000.

Antibodies can be immobilized by known means on a wide variety of insoluble support materials, both organic (e.g. U.S. Pat. No. 3,555,143, to Axen et al.) and inorganic (e.g. U.S. Pat. No. 3,652,761, to Weetall). Immobilization of the antibodies facilitates separation of the labeled composite from the excess labeled $T_4$. In a preferred embodiment, the antibodies are immobilized onto a high surface area, insoluble support, in particulate form, having an average particle size (e.g. 0.01 to 10 microns) which permits the carrier particle and attached antibodies to remain in suspension during the incubation period. The particles must not be too small, however, since it should be possible to separate the labeled composite using an available laboratory centrifuge. Thus, to be suspendable, the composite should utilize glass particles having an average particle size ranging from about 0.01 to about 10 microns.

Although other carriers can be used, a preferred carrier is an arylamine derivative of silanized porous glass particles having an average particles size of about one micron (for suspendibility and centrifugation). Porosity of the glass assures a high surface area for relatively high loading of the antibody. In the examples, the average pore diameter of the carriers used was about 550A. The anti-TBG was fixed onto the surface of the arylamine derivatized glass particles by diazotizing the arylamine surface and then reacting that diazotized surface with a solution of the antibodies by known means.

The TBG was obtained by extraction from defibrinated human plasma and it was purified by the method of Marshall, J. S. and Pensky, J. Arch. Biochem. Biophys. 146, 76 (1971).

The radiolabeled $T_4$ used ($I^{125}$ $T_4$) is that commercially available (Item No. 474035, Biological Products Dept., Corning Glass Works, Medfield, Mass.).

Patient serum samples were obtained from a local source. They included samples from "normal" patients and several with suspected thyroid dysfunction. Serum with low TBG values (2 to 3 $\mu$g/ml) was obtained as a by-product of the above extractions.

Very broadly, my method of using the immobilized anti-TBG to determine the TBG concentration in a blood serum sample comprises four basic steps: (1) reaction (incubation) of the reagent with TBG of the sample, (2) reaction (incubation) with the labeled $T_4$; (3) separation of the reagent complex; and (4) counting. In the first step, the reagent is incubated with a serum sample under conditions sufficient to assure complexation of substantially all TBG present in the sample to the antibodies of the reagent. The amount of composite per unit sample must be such that substantially all TBG is taken up by the composite. As a very practical matter, it has been found that for a 1 $\mu$l sample, substantially all TBG is complexed if at least about 0.5 mg of the composite described above is used.

After the TBG is complexed to the composite, it was found, surprisingly, that the TBG was still capable of complexing further with labeled $T_4$. Thus, by using labeled $T_4$ (e.g., $I^{125} - T_4$), it became possible to label at least a portion of the TBG complexed, thus providing a direct marker related to the amount of TBG in the original sample. After the complexed TBG is so labeled, it is separated from the non-complexed (remaining) labeled $T_4$ (e.g. by centrifugation) and counted. Alternatively, the remaining labeled $T_4$ may be counted. The ultimate count can be related to TBG concentration via preparation of and correlation with a standard curve. Since the uptake of a known amount of labeled $T_4$ is directly related to the amount of TBG complexed with the reagent (and originally in the sample), the method disclosed herein provides a substantially direct TBG measurement via use of a standard curve.

It should be noted that the labeled $T_4$ can be added to the reagent before or after addition and incubation of the serum sample. As indicated below, the sequence of labeled $T_4$ addition had no effect on the accuracy of results. An advantage in mixing the labeled $T_4$ with the reagent prior to sample incubation is that both the reagent and label can be provided in a single test tube (unit tube) requiring only the addition of the sample, incubation, separation, and counting. In other cases, because of possible damage caused by the radioactive label and/or short half life, it may be desirable to keep the labeled $T_4$ separate from the reagent. In that case, the label can be added just prior to or just after the addition of the serum sample.

The overall procedure can be schematically represented as follows where the immobilized antibody (anti-TBG) is represented by IMA, and $T_4^*$ represents the radiolabeled thyroxine.

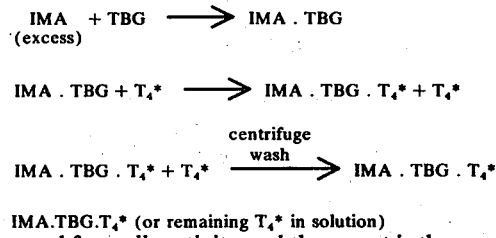

IMA.TBG.$T_4^*$ (or remaining $T_4^*$ in solution)    4.
is counted for radioactivity and the count is then correlated to a standard curve relating TBG concentrations to similar counts.

In the illustrative examples below, a detailed description is given for the preparation of a standard curve covering TBG values of a clinically significant concentration range. Also, an example is given describing one method of measuring TBG values of patient serum samples. The method is also shown to work with unit tubes (prefilled with IMA and $T_4^*$). Further experiments showing the effects of various dilutions and serum interference are described.

Preparation of Standard Curve

Several antigen (TBG) concentrations are chosen over the accepted normal range and including hypo and hyper levels. A typical series might be 1, 2, 4, 8, 16, 32, 64 and 128 micrograms ($\mu g$) of TBG per ml of solution. One $\mu l$ of each is added to tubes containing a suspension of one milligram of immobilized antibody (IMA) in a 0.5 ml aqueous solution. The IMA-antigen mixture is incubated for about 20 minutes within a temperature range of 22° C. to 37° C. After the incubation period about one ml of 0.85% saline is added, vortexed briefly, and centrifuged for three minutes at about 1000 rpm. The supernatant liquid is discarded. To the tube is then added about 0.5 ml of $I_{125}$ labeled thyroxine ($T_4^*$) containing approximately 20,000 cpm. A second incubation period as before is adequate to bind the radiolabeled thyroxine to the TBG sample which was previously complexed to the immobilized anti-TBG. Thus, total time for both incubations is less than 60 minutes. The saline wash and centrifugation are repeated as before. The retained activity in each tube is calculated as a percentage of the maximum activity bound (B/B max). This data is plotted on semi-log paper versus antigen (TBG) concentration in $\mu g/ml$ of sample. A typical standard curve is shown in FIG. I. Alternatively one may employ a linear-log plot of % bound vs. increasing TBG concentrations.

EXAMPLE I (Patient-Serum Samples)

Typical assays are illustrated by the following steps:
1. To a 12 × 75 mm assay tube is added an amount of immobilized anti-TBG (IMA) sufficient to bind with all of the antigen (TBG) in the sample to be assayed. In the present case one milligram of IMA contained enough antibody to combine with up to 100 nanograms of the TBG.
2. Next, the sample is added containing an amount of serum compatible with step (1). In this example one microliter was used (dilutions can be made and larger volumes used).
3. The IMA-TBG mixture is then incubated for about 20 minutes within at temperature range from 22° C. 37° C.
4. After the incubation period, about one milliliter of 0.85% saline wash solution is added, vortexed briefly and centrifuged for three minutes at about 1000 rpm. The supernatant liquid is discarded.
5. To the tube is then added about 0.5 ml of $I_{125}$ labeled thyroxine ($T_4^*$) containing approximately 20,000 cpm.
6. A second incubation period of about 20 minutes at a temperature ranging from 22° C. to 37° C. is adequate to bind the radiolabeled thyroxine to the TBG sample which was previously (step 3) complexed to the immobilized anti-TBG.
7. The saline wash and centrifugation are repeated as in step (4).
8. The retained radioactivity is then determined in a gamma scintillation counter and the concentration of TBG in the serum sample is read directly from a standard curve generated as described above.

Example II (Extended incubation time with prefilled unit tubes)

In this example the same quantities of IMA and antigen (known amounts of TBG) are placed in a series of tubes for the preparation of the standard curve. The $T_4^*$ is also added at this time to this series of tubes.

In addition to the above steps used to prepare tubes for the standard curve, several tubes are prepared and labeled as patient's sample to be assayed using the same samples as in Example I. To these tubes are added only the IMA and the $T_4^*$. All tubes were maintained at 5° C. for 18 hours. After 18 hours the patient serum samples were added to the prepared tubes and all tubes incubated at 37° C. for 30 minutes followed by a saline wash and centrifugation as before. The relative concentrations of TBG found in the patient samples were in general agreement with those found in Example I. The results of this example and the results of Example I are compared in Table I.

TABLE I

| Patient Serum Saple No. | TBG FOUND (μg/ml) | |
| --- | --- | --- |
| | Example I | Example II |
| 1 | 2.2 | 1.9 |
| 2 | 7.4 | 5.8 |
| 3 | 6.9 | 6.8 |
| 4 | 1.9 | 2.2 |
| 5 | 13.0 | 8.3 |

TBG (Antigen) Dilution and Recovery

A TBG standard containing 100 μg of TBG/ml of solution was diluted through a series of 1:2 dilutions producing samples containing 50, 25, 12.5 and 6.25 μg TBG/ml. These samples were assayed as in Example I. The results (see Table II) describe a linear relationship.

TABLE II

| Saple | TBG Concentration in μg/ml | | % Recovery |
| --- | --- | --- | --- |
| | Calculated | Found | |
| 1 | 50 | 51 | 102 |
| 2 | 25 | 27.3 | 109 |
| 3 | 12.5 | 12.7 | 102 |
| 4 | 6.25 | 6.3 | 102 |

Figure 2:
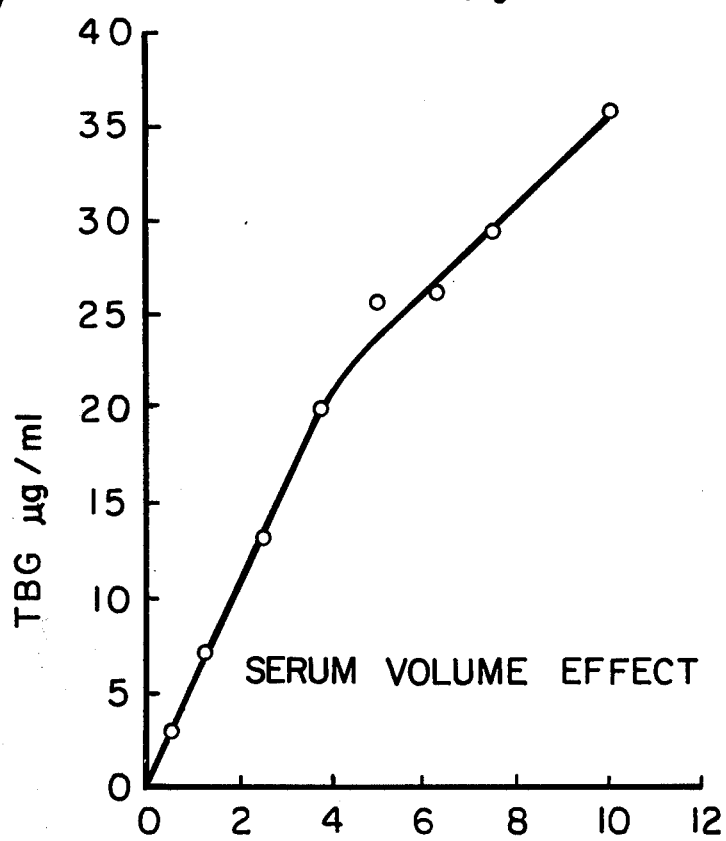
FIG. 2 is a graph illustrating the effect of serum volume on linearity of a standard curve.

Serum Interference With Linear Recovery:

Using human serum having a low TBG concentration, a series of samples with increasing serum volume and test tube volumes held constant with buffer was assayed for TBG as in Example I. A linear response is found if less than 5 μl of serum is used in the assay. (See FIG. 2.) This indicates there was no interference by serum constituents until the serum volume exceeds about 5 μl. Additional experiments showed that the assay of TBG according to this disclosure was independent of serum thyroxine levels ranging from about 10 to 400 ng/ml.

Given this disclosure, it is thought that the reagent and method disclosed herein is subject to various modifications within the spirit of this invention. Accordingly, it is intended that the invention disclosed herein should be limited only by the following claims.

I claim:

1. A method of determining the concentration of thyroxine binding globulin is a fluid sample, the method comprising the steps of:

A. incubating the sample with i. a composite comprising antibodies to thyroxine binding globulin immobilized on an insoluble carrier material, the incubation being under conditions, and with composite quantity sufficient to complex substantially all thyroxine binding globulin in the sample onto the antibodies of the composite; and ii. a quantity of radiolabeled thyroxine in a quantity sufficient to complex with at least a portion of the thyroxine binding globulin complexed to the antibodies of the composite;

B. separating the composite and materials complexed thereto from unbound radiolabeled thyroxine;

C. counting the radioactivity of the separated composite or the remaining radiolabeled thyroxine; and D. correlating the count of step (C) with a standard curve relating concentrations of thyroxine binding globulin to counts of the type determined by step (C).

2. The method, as claimed in claim 1, wherein the incubation of step (A)(ii) is subsequent to the incubation of step (A)(i).

3. The method of claim 1 wherein the composite comprises antibodies to thyroxine binding globulin fixed on the surfaces of an inorganic carrier.

4. The method of claim 3 wherein the inorganic carrier comprises glass particles which, with the antibodies fixed thereon, are suspendable in the incubation medium.

5. The method of claim 1 wherein the radiolabeled thyroxine is labeled with $I^{125}$.

6. The method of claim 1 wherein the total incubation time of step A is less than about 60 minutes.

7. A reagent for determining the concentration of thyroxine binding globulin in a fluid sample, the reagent being an immunochemical composite comprising antibodies to thyroxine binding globulin attached to the surfaces of an essentially water insoluble carrier material.

8. The reagent of claim 7 wherein the carrier material is inorganic.

9. The reagent of claim 8 wherein the carrier consists of silanized glass particles.

10. The reagent of claim 9 wherein the particles are suspendable in an aqueous solution and have an average particle size ranging from about 0.01 to 10 microns.

11. The reagent of claim 10 wherein the glass particles are porous.

* * * * *